(12) United States Patent  
Levinson et al.

(10) Patent No.: US 9,034,360 B2  
(45) Date of Patent: May 19, 2015

(54) BIOGENERATOR CONSTRUCTED USING LIVE CELL CULTURES

(71) Applicant: Simon Rock Levinson, Denver, CO (US)

(72) Inventors: Simon Rock Levinson, Denver, CO (US); Joseph Bango, New Haven, CT (US)

(73) Assignee: Biotricity Medical, Inc., Hopkinton, MA (US)

( * ) Notice: Subject to any disclaimer, the term of this patent is extended or adjusted under 35 U.S.C. 154(b) by 0 days.

(21) Appl. No.: 13/940,191

(22) Filed: Jul. 11, 2013

(65) Prior Publication Data

US 2013/0323535 A1     Dec. 5, 2013

Related U.S. Application Data

(63) Continuation of application No. 12/296,962, filed as application No. PCT/US2007/066642 on Apr. 13, 2007, now abandoned.

(60) Provisional application No. 60/791,829, filed on Apr. 13, 2006.

(51) Int. Cl.
*A61F 2/00* (2006.01)
*H01M 8/16* (2006.01)
*A61N 1/378* (2006.01)
*C12M 3/00* (2006.01)

(52) U.S. Cl.
CPC .......... *H01M 8/16* (2013.01); *A61B 2560/0214* (2013.01); *A61N 1/3785* (2013.01); *C12M 23/44* (2013.01); *Y02E 60/527* (2013.01)

(58) Field of Classification Search
CPC ...... A61N 1/3785; H01M 8/16; C12M 23/24; A61B 2560/0214; Y02E 60/527
See application file for complete search history.

(56) References Cited

U.S. PATENT DOCUMENTS

2004/0241771 A1* 12/2004 Zeikus et al. ................ 435/7.32

OTHER PUBLICATIONS

Newton's Ocean (last viewed on May 4, 2012).*
Madara et al., A Simple Approach to Measurement of Electrical Parameters of Cultured Epithelial Monolayers: Use in Assessing Neutrophil-Epithelial Intractions., J. Tiss. Cult. Meth., (1992), vol. 14, pp. 209-216.*
Truschel et al., Primary Uroepithelial Cultures, The Journal of Biological Chemistry, 1999, vol. 274, pp. 15020-15029.*
Guide to Ussing Chamber System, A Harvard Apparatus Company (last viewed on May 4, 2012).*
Ussing_chamber (last viewed on May 7, 2012).*
Greenwood et al. (Membrane potential difference and intracellular cation concentrations in human placental trophoblast cells in culture, Journal of Physiology (1996), vol. 492, pp. 629-640.*

(Continued)

*Primary Examiner* — Alexander Kim
(74) *Attorney, Agent, or Firm* — Swanson & Bratschun, L.L.C.

(57) ABSTRACT

An apparatus (or a biogenerator) is disclosed which utilizes the electrochemical polarization of epithelial cells to generate electricity. The apparatus employs living cells to convert chemical energy into electricity. The biogenerator is capable of supplying electricity to other devices continuously for extended periods of time. Because the apparatus may be made sufficiently small for implantation into the body of an animal or a human, such an apparatus is particularly useful for powering devices that require implantation into the host body.

5 Claims, 6 Drawing Sheets

(56) References Cited

OTHER PUBLICATIONS

Rojanasakul et al. (The Transport Barrier of Epithelia: A Comparative Study on Membrane Permeability and Charge Selectivity in the Rabbit., Pharmaceutical Research, vol. 9, pp. 1029-1034.*

Getchell et al., Electrogenic Sources of Slow Voltage Transients Recorded From Frog Olfactory Epithelium, J Neurophysiol. (Nov. 1974), vol. 37(6), pp. 1115-1130.*

Bertrand et al., System for Dynamic Measurements of Membrane Capacitance in Intact Epithelial Monolayers., Biophysical Journal (1998), vol. 75, pp. 2743-2756.*

* cited by examiner

BIOGENERATOR CONSTRUCTED USING LIVE CELL CULTURES

RELATED APPLICATIONS

This application claims priority of pending U.S. patent application Ser. No. 12/296,962, filed Dec. 30, 2008, entitled "Biogenerator Constructed Using Live Cell Cultures" which application is a 35 U.S.C. §371 national phase application of PCT/US2007/066642 (WO2007/121359), filed on Apr. 13, 2007, entitled "Biogenerator Constructed Using Live Cell Cultures", which application claims the benefit of U.S. Provisional Application Ser. No. 60/791,829, filed Apr. 13, 2006, which are each incorporated herein by reference in their entirety. Any disclaimer that may have occurred during the prosecution of the above-referenced application(s) is hereby expressly rescinded, and reconsideration of all relevant art is respectfully requested.

BACKGROUND

1. Field of the Invention

The present invention relates generally to the field of power generation using biological materials. More specifically, the disclosed apparatus and method utilize electrochemical polarization of epithelial cells to generate electricity. Living cells are used to convert chemical energy into electricity. The apparatus is capable of providing long-lasting power to other devices continuously over an extended period of time. Such an apparatus is particularly useful for powering devices that are implanted in the body of an animal or a human, where it may utilize metabolites provided by the host to produce electrical energy without the need for external fuel sources.

2. Description of Related Art

Batteries that utilize biological materials as an integral component are dubbed "biobatteries." However, it is more appropriate to describe some of these devices as "biogenerators" because they produce electrical power from external sources of continuously supplied biochemical substrates. Although the first such enzyme based device was created in 1964, the underlying principles of operation remain the same. Briefly, enzymes are immobilized onto the anode and/or cathode, which are immersed into an electrolyte containing specific substrates for the enzymes. Chemical reactions occurring at the anode result in loss of electrons by the reactants, while reactions at the cathode result in a net gain of electrons. Thus, a voltage potential is generated between the anode and the cathode. Electrons flow from the anode to the cathode when the two poles are connected, as generally described in Mano et al., A miniature biofuel cell operating in a physiological buffer, J. Am. Chem. Society, 124: 12962-63 (2002).

There is a need to reduce the size of biobatteries while also increasing their service life. Although Mano et al. reported miniaturizing their biobattery while generating about 1.9 mW of electric output at 0.52 V, the battery only lasts for about a week. This relatively short life span may be attributed to the limited supply of substrates inside the battery. For example, the battery designed by Mano et al. uses glucose as a substrate. The battery ceases to produce electricity when the glucose contained inside the battery is depleted. Furthermore, the enzyme-coated electrodes steadily deteriorate and themselves have a limited lifespan.

Another line of research focuses upon cutting the cost of the biobattery/biogenerator. As a result, new types of batteries have been developed which enlist living cells to power the underlying reactions. In one study, live bacterial cells are used in place of more expensive enzymes to catalyze the reactions inside the biogenerator. See e.g., Graham-Rowe, Food scraps could help power homes, New Scientist, issue 2364, Oct. 12, 2002. Although this bacteria-based device may be cheaper to make and could function as a biogenerator using host nutrients, the size of these batteries is close to that of a Walkman cassette player. This size is problematic, for example, in that the size largely precludes use for implantation purposes. Moreover, the use of live bacteria may raise some health concerns when implantation in the host is required.

Many problems remain to be solved before putting these devices into practical use. For biobatteries, both the size and the life span of the device limit the its use as a power source, especially for applications that require implantation of the battery into the human body. For biogenerators, the inclusion of non-human cells such as bacteria in the biogenerator may cause adverse immune response by the host. Therefore, there is a need for a small-sized biogenerator that produces electricity over an extended time without using bacterial cells.

SUMMARY

The presently disclosed instrumentalities overcome the problems outlined above and advance the art by utilizing specialized live cells to generate electricity. The live cells are capable of establishing a transcellular voltage by transporting ions across the membranes of the cells. The cells are cultured as monolayers so that a uniform polarization can be created. Each monolayer is in essence a mini-battery on its own. Multiple monolayers of cells may be stacked inside a cell culture chamber to form a tandem array of mini-batteries. This arrangement helps increase the operating voltage and total power output from the apparatus while permitting the device to occupy a relatively smaller volume or footprint than is obtainable from prior art devices having the same output characteristics. The device is preferably called "a biogenerator," rather than "a biobattery," since the device uses externally supplied energy sources to produce large amounts of electrical energy over a long service life.

According to this disclosure, the live cells are preferably epithelial in origin. More preferably, the live cells resemble the epithelial layer of the tubule of the kidney nephron. It is further disclosed that transgenes coding for ion transporting proteins, such as ion channels and ion pumps, may be introduced into the epithelial cells in order to create a more powerful ion-transporting machinery and to increase both the voltage and current across the cell membrane.

The apparatus is also capable of providing long-lasting power for other devices. Immortal cell lines are preferred because they may perpetuate epithelial monolayers. In one embodiment, the cell culture chamber is embedded inside the host body. Nutrients and oxygen may be drawn from the host and waste may be excreted into the blood stream of the host. Under ideal conditions, it is possible that the biogenerator according to this disclosure may last for as long as the host is living.

DETAILED DESCRIPTION

In one aspect, the disclosed apparatus may utilize the transmembrane voltage and ion currents created by live cells to generate electricity. The apparatus is an improved biogenerator, and the terms biogenerator and apparatus may be used interchangeably throughout the disclosure. In one embodiment, the biogenerator may function by providing electricity in real time to any device in need of electricity. In another embodiment, the biogenerator may be connected with another device capable of storing electricity, such as a capacitor. In this mode, the biogenerator may be operated as part of a battery, or biobattery to reflect that the electricity is generated by live cells. The capacitor may be designed to be an integral part of the apparatus. However, the addition of the capacitor may significantly increase the size of the apparatus, and may thus limit the use of the apparatus in vivo.

Manner of Operation

The live cells are preferably immortalized epithelial cells, but other adhesion cell types, such as fibroblasts, may also be used if the cells are modified such that they form structures which functionally mimic the ion transport properties of an epithelium. In certain epithelial cells, such as those of the kidney involved in regulating body water and electrolyte balance, or those involved in absorbing nutrients from the gut, ion transporting proteins are usually distributed non-uniformly in the plasma membrane. For instance, in kidney tubules, energy-requiring $Na^+$ pumps are located exclusively on the basolateral side of the plasma membrane (i.e. that facing the serosal side of the epithelia) while passive $Na^+$ channels are found on the apical side of the epithelium, i.e. that lining the tubule lumen.

Figure 2:
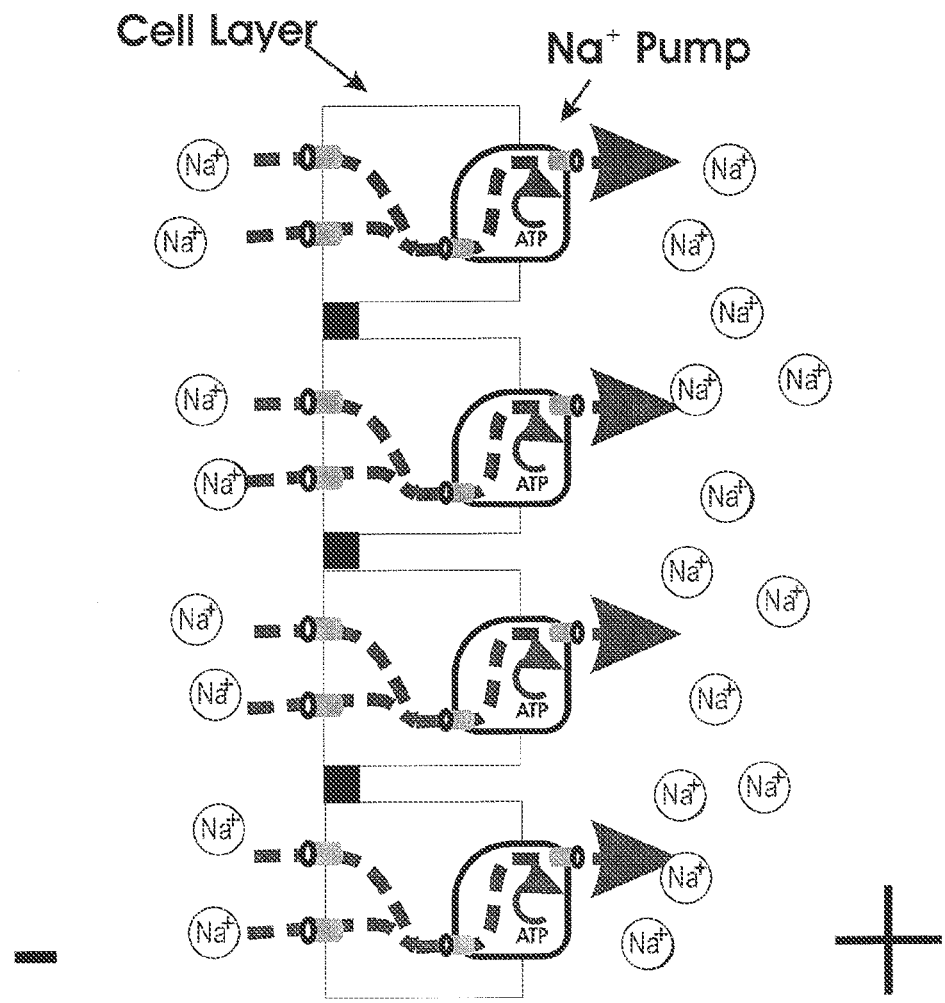
FIG. 2 shows ionic transport across an epithelial monolayer that may be utilized in biogenerator devices.

Kidney tubule epithelia transport sodium ions through their cells via the action of $Na^+$ pumps, which are protein complexes that use ATP as energy to transport ions against the gradients. While the biological purpose of this transport is to regulate the composition of ions within the body, a quantifiable generation of electrical energy results in the form of an ionic current and a voltage across the epithelial cell layer. Thus the basolateral pumps extrude sodium ions from within the cell to the serosal side of the epithelia. This creates a deficit of ions within the cell, thus attracting the entry of sodium ions from the luminal side of the epithelia through $Na^+$ channels in the apical membrane. This primary basolateral pumping of sodium ions thus creates a flow of positive charge (i.e. $Na^+$) across the entire cell layer. The resulting accumulation of sodium on the serosal side makes it electrically positive. Hence electrical energy results in the form of a transepithelial voltage and a flow of ionic current through a cell layer due to what may be called a sodium pump, as shown in (see FIG. 2). This action is described generally in, Molecular Biology of the Cell. 4th ed., B. Alberts et al., Chapter 11 (Garland Publishing, 2002), which is hereby incorporated by reference to the same extent as though fully replicated herein. This electrical power may be harnessed and amplified by the instrumentalities described herein.

The amplitude of the voltage potential produced by such transepithelial ion transport is determined by multiple factors. Primary among these is the relative abundance of the $Na^+$ ion transport mechanisms in the basolateral and apical membranes. Naturally as the density of such molecules increases in the cell membranes, then the greater the $Na^+$ ion current, the larger the transepithelial voltage and thus the larger the power produced by the epithelial layer. Thus, to increase this density in the live cells to be used in the biogenerator, these cells may be transected with foreign genes that code for ion channel and ion pump proteins to further increase the voltage potential each cell produces. Foreign genes refers to both genes that are not naturally present in the genome of the cells to be transected or those that are present but due to intrinsic regulation by the cell are either not normally expressed or are expressed at lower levels than required for optimal operation of the biogenerator. Examples of such genes include those encoding the isoforms of the epithelial sodium channel ENaC in various species and those encoding various isoforms of the Na/K-ATPase ion pump. It also includes genes encoding aldosterone receptors that when complexed to aldosterone increase the expression and activity of endogenous forms of these channels and pumps.

Another factor that has substantial effect on the cross-membrane voltage is the electric seal between adjacent epithelial cells. The transepithelial voltage potential and ionic current may be substantially reduced if this seal is relatively leaky. Such leaks are deleterious to electricity generation because they allow transported $Na^+$ to return to the luminal side of the epithelium, thus effectively short-circuiting the electricity-generation process. Alternatively, these intercellular leaks may allow the transepithelial passage of negatively-charged counterions such as chloride ($Cl^-$) to accompany active $Na^+$ transport; in this case each co-movement of a $Cl^-$ ion electrically neutralizes the effect of transport of one $Na^+$.

Figures 1, 1A:
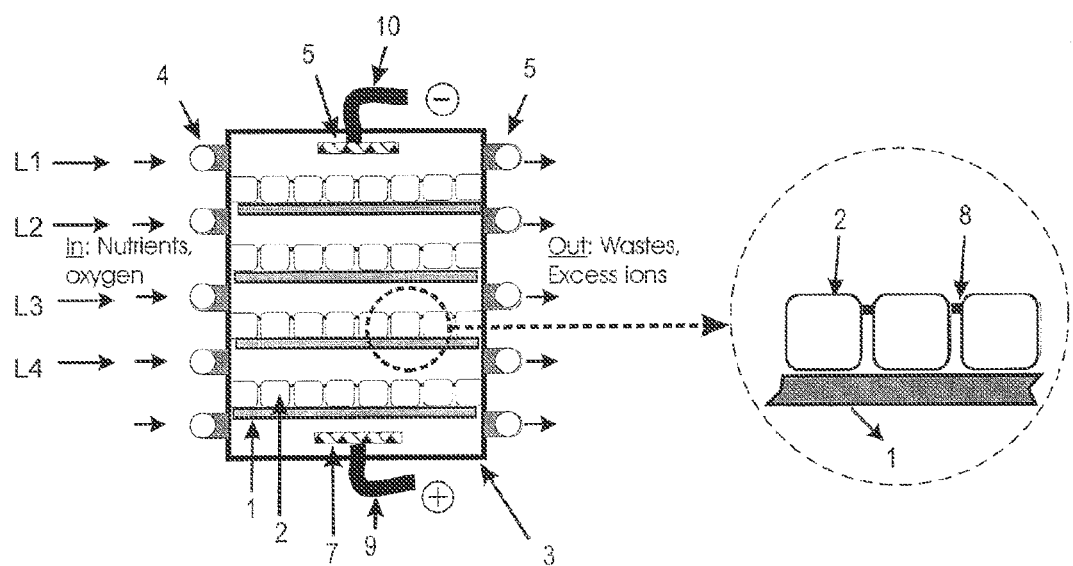
FIG. 1 depicts the general configuration of one biogenerator according to the present disclosure.
FIG. 1A is a balloon showing expanded detail with respect to an aspect of FIG. 1.

In both natural and artificial epithelium, a seal between adjacent epithelial cells is achieved by structures called tight junctions 8, which prevent ions from flowing freely from one side of the epithelium to the other (see FIG. 1). In some epithelial cells, the permeability of their tight junctions to certain solutes and water may be regulated by the cells. See generally, Molecular Biology of the Cell. 4th ed., B. Alberts et al., Chapter 19 (Garland Publishing, 2002). Different types of tight junctions may have different degrees of permeability to various solutes. For instance, tight junctions in the epithelium lining the small intestine are ten thousand times more permeable to inorganic ions, such as $Na^+$, than the tight junctions in the epithelium lining the kidney tubule epithelium or the urinary bladder. These differences are attributed to the protein composition of the tight junctions. Therefore, transgenes encoding tight junction proteins typical of those found in these latter electrically "tight" inner linings of the kidney tubules or urinary bladder may be introduced into the live cells of the present invention to enhance the electric seal, hence increase bioelectricity production by each layer of the artificial epithelia biogenerator. Examples of such genes include those encoding the claudin isoforms, annexin A2, ZO-1, and other proteins thought to increase transepithelial electrical resistance through tight junction formation.

Technical Description:

The live cells comprising the artificial epithelial layers may be long-lived, in order to supply power over an extended period of time. In addition, such artificial layers may have the property of being self-repairing, i.e. when gaps in the layer form due to natural cell death, then surrounding cells will replicate to fill in the gap. Naturally occurring immortal cell lines or cells that have been made immortal by genetic engineering that spontaneously form epithelial monolayers in culture are preferred. Examples of such cells include established cell lines such as MDCK, MDBK, RIMCT, OMK, OPK, or A6 cells and their derivatives or other cell lines to be developed in the future. In addition, human stem cells may be used to differentiate into normal epithelial cells, such as those of kidney tubules to form the monolayers used in the device.

Cloning these genes into the cells of interest may be done by techniques that are generally known in the art of molecular genetics. One such example of these techniques is described in Chan, Wang, Liu and Pearce, *Aldosterone responsiveness of A6 cells is restored by cloned rat mineralocorticoid receptor*, American Physiological Society (1998) (Article 0363-6143/98), which is incorporated by reference to the same extent as though fully replicated herein.

The term "derivative" means cells that are derived from a particular cell type. For example, one cell line may result from the fusion of two other cell lines. Alternatively, a cell line may result from transformation of another cell line. Genes may also be artificially introduced into a cell line to alter its type or its behavior. Derivatives may also be created by subjecting a cell line to physical or chemical elements to induce mutations.

In order to grow in the polarized epithelial monolayer configuration used in the biogenerator, the cells of the present disclosure require attachment to a special supporting substrate. Because the transepithelial voltage and current results from the collective ion transport of many cells, it is useful that such cells form a uniform and fixed polarity. As shown in FIGS. 1 and 1A, live cells 2 are grown on permeable supports 1, inside a cell culture chamber 3. The live supports 1 are preferably structures capable of supporting formation of single epithelial cell layers when seeded by immortal epithelial cell lines, and are commercially available, e.g. as Snap-Well™ inserts, from Corning, Inc. Each chamber may contain more than one epithelial cell monolayer, each grown on its own support where, for example, four such layers L1, L2, L3, L4 are shown in FIG. 1. In a preferred embodiment, as shown in the multilayer configuration of FIG. 1, the epithelial cell layers are stacked in electrical series, hence the transepithelial potentials produced by each layer sum with one another to produce a total voltage. This is a preferred mode of the proposed biogenerator because the transepithelial voltages produced by a single artificial layer are typically less than 0.1V and thus inadequate to activate current solid-state microcircuits, which typically have minimum operating voltages of 0.3-0.5V.

Preferably, the chamber is connected with the tissue environment of the host through fluid flow ports including inlets 4 and outlets 5, so that nutrients and oxygen contained in body fluids, such as blood, may be used to support growth of the cells when implanted in the host body.

In one aspect, the live supports 1 may be constructed to present geometries for the densification of power output, i.e., so that the device occupies a smaller volumetric or areal footprint for a given power output. If the biogenerator is to be embedded in a host, it is desirable to maximize the power/volume ratio, which is the ratio between the power that the apparatus generated and the size of the biogenerator. One strategy for enhancing the power/volume ratio may be to increase the surface area of the monolayer by growing the cells on rippled or highly infolded or invaginated surfaces. Another approach may be to grow them in tiny hollow fiber tubes (not shown) such as those typically used in renal dialysis.

If the biogenerator is to be used without being embedded in a host body, the appropriate commercially available cell culture media may be used to maintain cell growth (e.g. DMEM, fetal calf serum).

Preferably, the contents of the cell culture chamber is separated from the host tissue environment via a semipermeable barrier that prevents contact between immune cells of the host with the biological materials (especially cells) of the biogenerator. The barrier may be made from biological or man-made materials. Ideally, the barrier allows nutrients, oxygen, carbon dioxide and other gases to pass freely, while blocking the passage of cells in either direction. This latter feature is useful to prevent contact of the immune system of the host with the foreign cells of the biogenerator and the possibility of subsequent immunorejection of the implanted device.

In another aspect of the present disclosure, stem cells may be obtained from the host to form the biogenerator monolayers, the possibility of immune rejection of the implant by the host may be eliminated or mitigated, as is the need to incorporate a semipermeable barrier into the design of the device. Stem cells may be cultured and induced to differentiate into a variety of cell types. By way of example, these documents that are hereby incorporated by reference to the same extent as though fully replicated herein to illustrate various aspects in the use of stem cells: Gupta S, Verfaillie C, Chmielewski D, Kren S, Eidman K, Connaire J, Heremans Y, Lund T, Blackstad M, Jiang Y, Luttun A, Rosenberg M E. Isolation and characterization of kidney-derived stem cells. J Am Soc Nephrol. 2006 November; 17 (11):3028-40; see also Levy Y S, Stroomza M, Melamed E, Offen D. Embryonic and adult stem cells as a source for cell therapy in Parkinson's disease. 1: J Mol Neurosci. 2004; 24(3):353-86. Differentiation of the stem cells into epithelial cells is preferred.

In another embodiment, waste materials, such as cell debris and metabolic waste may be processed within the biogenerator before being released into the host tissue environment or blood stream. In one aspect, proteases may be used to degrade cell debris and waste proteins Amino acids resulting from proteolytic degradation that are not harmful for the host may be released to the host.

For polarized $Na^+$-transporting epithelial layers, the biogenerator contains a cathode 6 and an anode 7. Electric wires 9, 10 connect the biogenerator to an electronic device (not shown). The electronic device may be one that is embedded in the body of an animal or a human, such as a pacemaker, artificial vision system, or hearing aid. Alternatively, the electronic device may be any stand-alone device that requires power supply. The preferred range of specific power output by the disclosed apparatus is from about 1 $\mu W$ per $cm^3$, with an operating voltage of at least 0.5V.

It is also useful to prevent the nutrient stream introduced into the chamber through inlets 4 from forming a short-circuit between layers of the biogenerator. Such a situation may occur since the nutrient stream, whether it be artificial cell culture media or bodily fluid from the host, contains a high concentration of ions and thus is a good conductor of electricity. Thus the inlet ports 4 through which nutrient fluids gain access to the chamber may be extended, small diameter structures with a high electrical resistance. Alternatively, the inlet ports 4 may contain valves that open only intermittently as needed to introduce metabolites or host fluids and to remove wastes and accumulated ions.

Figure 3:
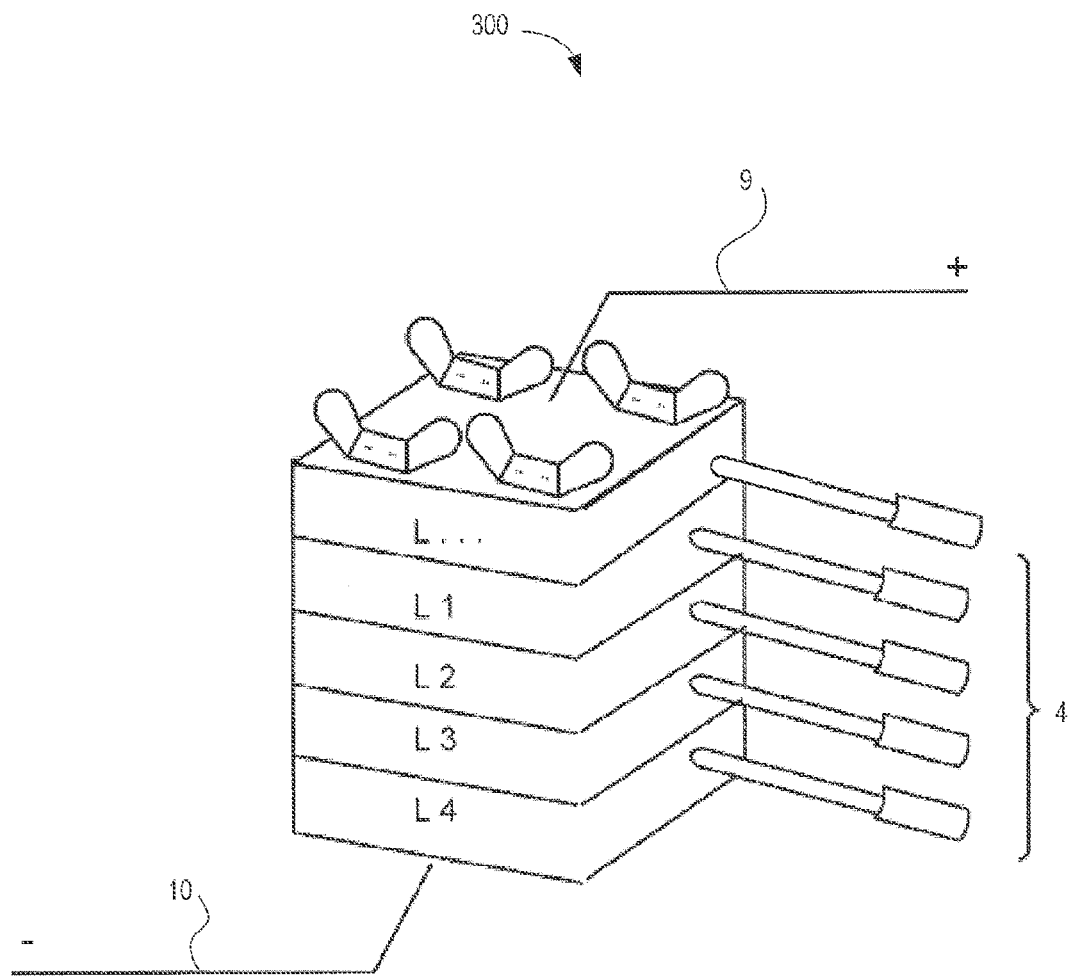
FIG. 3 shows one embodiment of a biogenerator.

As shown in FIG. 3, a biogenerator 300 may incorporate the features of FIG. 1 to provide a compact multilayer construction formed of layers L1, L2, L3, L4, which communicate with one another in electrical series between wires 9, 10. Any number of additional layers "L . . . " may be added to achieve a desired potential.

Figure 5:
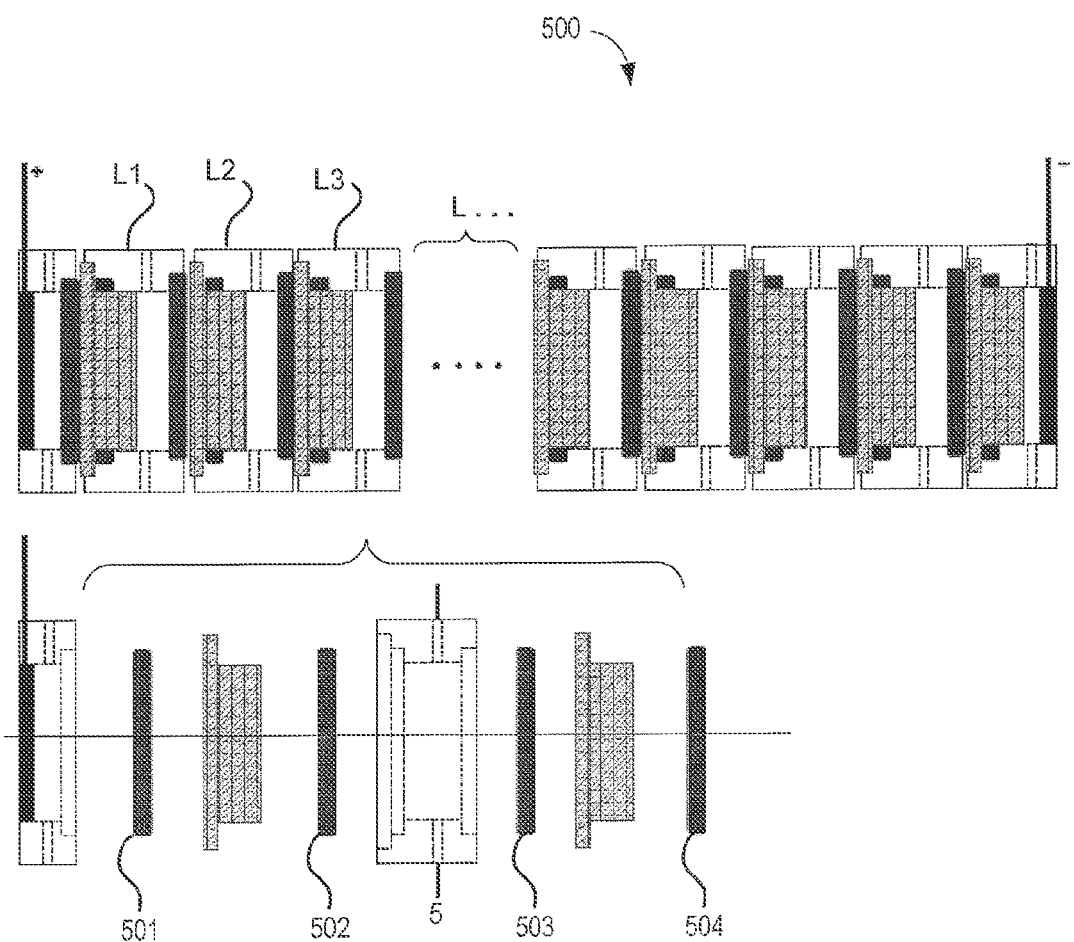
FIGS. 5 and 6 show the schematics of the prototype biogenerator used to construct the apparatus shown in FIG. 3 and to obtain the data in FIGS. 4A-D.

As shown in FIG. 5, a biogenerator 500 may contain any number of such layers L1, L2, L3, that are constructed and arranged in a manner permitting each layer to seal against adjacent layers. This may be done, for example, by providing O-rings 501, 502, 503, 504 to seal against snapwells 505, 506, and body 507 as shown. The body 507 may be provided with inlet 4 and outlet 5, functioning generally as shown in FIG. 1.

Figure 6:
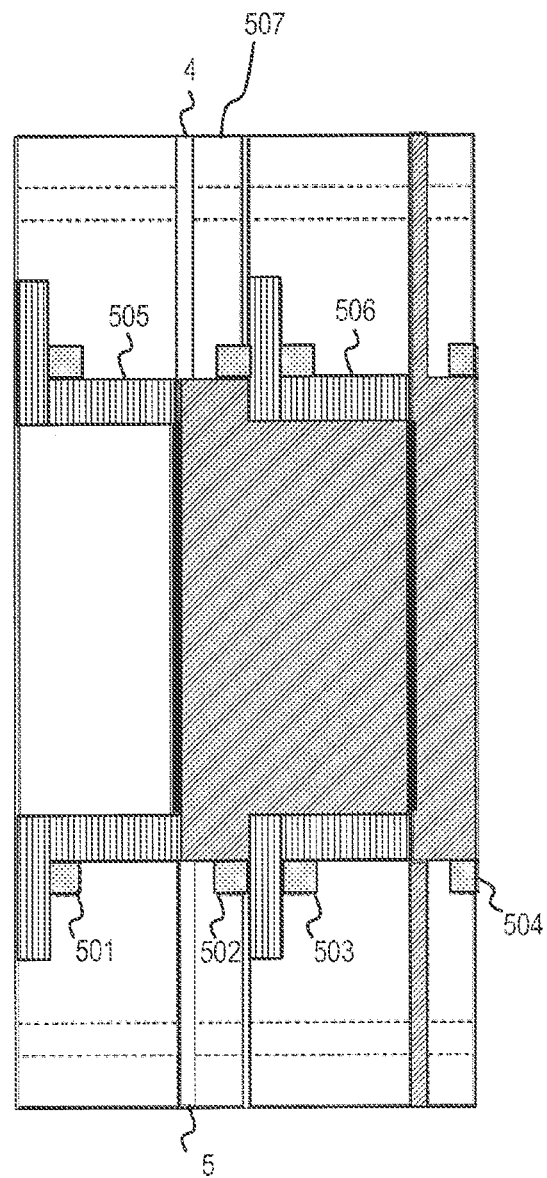

FIG. 6 provides additional detail as a midsectional view taken with respect to an aspect of FIG. 5. The O-rings 501, 502, 503, 504, are deployed as described above to seal snapwells 505, 506 against body 507. It will be appreciated that the body 507 is drawn to scale where the generally rectangular construction may be, for example, 30 mm by 7 mm. The ports 4, 5 may be suitably from 0.5 mm to 0.8 mm, with the inlet port 4 being approximately half the size of the outlet 5, or vice-versa. The outlet port 5 may be sized larger, for example, to encourage the removal of wastes or cellular debris, while the inlet may be sized smaller to deter entry unwanted materials. These dimensions are merely provided by way of example to show suitable dimensions according to one embodiment, and should not be unduly construed to limit what is claimed as the invention.

Practical Applications:

Electronic devices that may be powered by such a battery with a volume of a few $cm^3$ are primarily those that are normally implanted in an animal or human that replace, augment or monitor various biological functions or to treat disease. Primary among such devices would be cardiac pacemakers, artificial cochleas, vagal nerve stimulators for the treatment of epilepsy, and implanted insulin pumps to treat diabetes, and sensors to monitor vital signs of an animal or a human. Vital signs are biological parameters of a living organism. With respect to animals or humans, vital signs may include pulse rate, respiratory rate, body temperature, blood pressure, glucose levels and so on. For example, the biogenerator may be used to power a device that constantly record the electrocardiogram (EKG) of a living animal or human.

The electronic devices may also include instruments that enhance the senses of an animal, or more preferably, those of a human. For instance, the biogenerator may power an implanted device that enhance or restores a person's hearing or vision. Furthermore, the biogenerator may also be used to provide power for a pacemaker that requires constant and long-lasting power supply. Most implantable biomedical devices and sensors require low power by design. For instance, a pacemaker typically requires 1-10 μwatts to operate.

Comparison with Natural Fish Electric Organs

Although it has similarities in physical configuration, the biogenerator apparatus disclosed here differs functionally from the electric organ of electric fish in various aspects. Thus, while electric organs are capable of generating power output as high as 1 kW (or 1 $W/cm^3$), they can only do so for very brief periods of time, i.e. this high power output may only be created when hundreds of brief electrical spikes are discharged over a period of a few seconds. On the other hand, the present biogenerator is capable of providing relatively low but continuous power in which the epithelial cells according to the present disclosure operate in a continuous manner transporting ions across the membrane. Because the creation of bioelectricity in the disclosed device occurs constantly, the peak power output is much lower than that of the electric fish organ, but the actual power output averaged over long periods of time for the biogenerator is comparable to that of the electric organ.

It is to be understood that the following text teaches by way of example, and not by limitation. The instrumentalities disclosed herein are broader than the particular methods and materials used, which may vary within the skill of the art. It is also to be understood that the terminology used herein is for the purpose of describing particular embodiments only, and is not intended to be limiting. Scientific papers, review articles, patents and patent applications cited throughout this disclosure are hereby expressly incorporated by reference. Further, unless defined otherwise, all technical and scientific terms used herein have the same meaning as commonly understood by one of ordinary skill in the related art.

Example 1

A Prototypic Biogenerator with Three Monolayers of Cells Construction of Prototype Apparatus A biogenerator prototype was constructed as shown in FIG. 3 with connectors in place for the introduction of nutrient-rich media into each chamber. The material used for the individual chambers was Lucite, with coiled silver wire used for the electrodes. The initial apparatus consisted of three chambers to hold three artificial monolayers, with an electrode chamber on either end. The entire apparatus was held together with 4 stainless steel threaded rods Preparation of Epithelial Cell Monolayers:

Cultured A6 epithelial cells were used to power the biogenerator prototype. The cells were seeded onto commercially available Snapwell chambers (Corning Corp.) of about 1 $cm^2$ area and maintained until use with standard tissue culture media and conditions for this cell line (e.g. see Steele, R. E., Handler, J. S., Preston, A., and Johnson, J. P. (1992) *J. Tissue Culture Methods* 14, 259-264). Over a period of several days these cells spontaneously formed a packed epithelial monolayer on the polyester membrane of the Snapwell chamber. The development of the electrogenic properties of each monolayer was monitored using a specialized device (EVOM; World Precision Instruments, Inc.) until individual cultures produced significant voltages and electrical currents (e.g. 25 mV, 5 μA per 1 $cm^2$ monolayer area).

Recording of Electrical Characteristics:

Three mature A6 cell monolayers were placed in individual prototype chambers and the apparatus was assembled as shown in FIG. 5. A glucose-supplemented, buffered physiological salt solution was then introduced into the chambers through the ports shown in FIG. 3. The prototype electrodes were connected to a high impedance multimeter and the open-circuit voltage produced in the biogenerator prototype was measured frequently during the test procedures. FIG. 3 shows this configuration in which a biogenerator voltage of 92.5 mV was recorded.

Figure 4A:
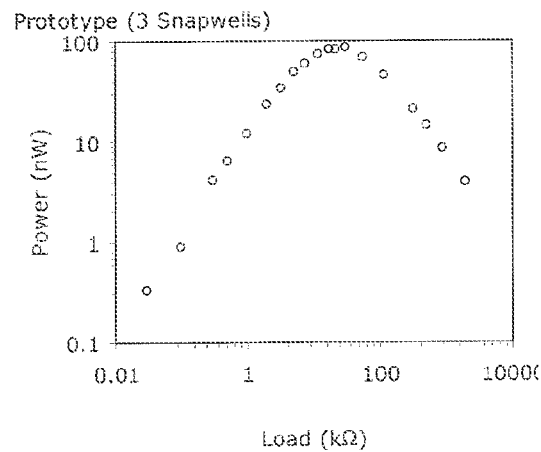
FIGS. 4A 4B, 4C, and 4D show the electrical characteristics data taken form a working embodiment of the biogenerator shown in FIG. 3.
Figure 4B:
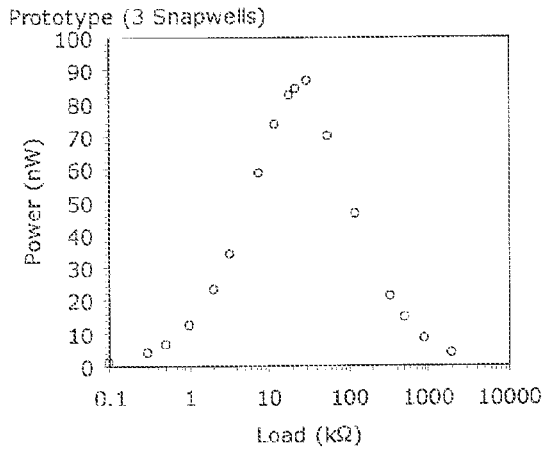
Figure 4C:
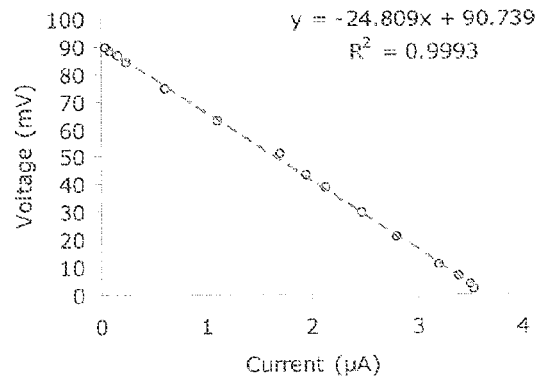
Figure 4D:
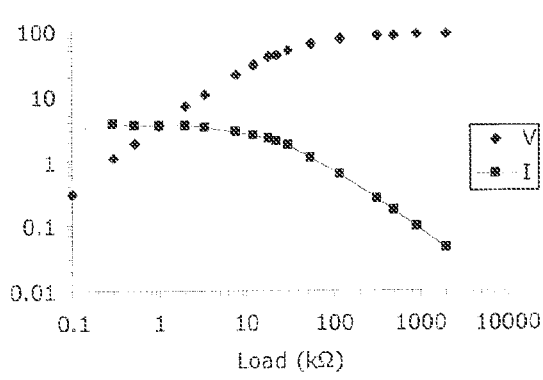

The power output of the biogenerator was then determined as a function of the electrical load placed on the device. To accomplish this, variable resistances were applied to the output of the device and the resultant voltage and electrical current across the load were measured. The data are graphically plotted as shown in FIGS. 4A through 4D. FIGS. 4A and 4B show the characteristic power-load relations for the device for respective logarithmic and linear power axes. It may be seen that the multilayer device produces about 90 nW (0.09 μW) of power under optimal load. FIGS. 4C and 4D show the voltage and electrical current produced under various load conditions. Overall, these test results show that adequate power output to drive various biomedical devices (e.g. power output at the required μW levels) may be obtained from about 30 monolayers.

What is claimed as the invention may be subjected to insubstantial changes without departing from the scope and spirit of what is described. Accordingly, the inventor hereby states his intention to rely upon the doctrine of Equivalents to protect what is claimed.

What is claimed is:

1. An apparatus comprising:
   at least one epithelial cell culture chamber wherein epithelial cells are maintained and grown to produce electricity by action of ion pumps and ion channels; and
   circuitry for harnessing the voltage and electrical current generated by the epithelial cells, said circuitry being connected with said epithelial cell culture chamber wherein the epithelial cells are an immortalized derivative of epithelial cells selected from the group consisting of MDCK, MDBK, RIMCT, OMK, OPK and A6.

2. The apparatus of claim 1, wherein the epithelial cells are capable of generating a transcellular voltage potential and an ionic current.

3. The apparatus of claim 2, wherein the transcellular voltage potential is generated through cross-membrane transport of ions by the epithelial cells.

4. The apparatus of claim 1, wherein the epithelial cells have been manipulated to produce ion pumps on one side of the cells and ion channels on the other side of the epithelial cells.

5. A biogenerator apparatus comprising:
   at least one epithelial cell culture chamber wherein immortalized epithelial cells are maintained and grown;
   said epithelial cell culture chamber comprising a stack of at least two layers connected in electrical series to increase output voltage and total power output;
   said immortalized epithelial cells being grown as a polarized monolayer on each layer; and
   a circuitry for harnessing the voltage and electrical current generated by the immortalized epithelial cells, said circuitry being connected with said epithelial cell culture chamber.

* * * * *